(12) United States Patent
Berger

(10) Patent No.: US 8,380,319 B2
(45) Date of Patent: Feb. 19, 2013

(54) ELECTRICAL SCREW

(76) Inventor: J. Lee Berger, Franklin Lakes, NJ (US)

( * ) Notice: Subject to any disclaimer, the term of this patent is extended or adjusted under 35 U.S.C. 154(b) by 1247 days.

(21) Appl. No.: 12/071,412

(22) Filed: Feb. 21, 2008

(65) Prior Publication Data

US 2008/0255556 A1 Oct. 16, 2008

Related U.S. Application Data

(60) Provisional application No. 60/907,622, filed on Apr. 11, 2007.

(51) Int. Cl.
*A61N 1/05* (2006.01)
(52) U.S. Cl. ............... 607/51; 607/50; 607/37
(58) Field of Classification Search ............. 607/51, 607/50, 37
See application file for complete search history.

(56) References Cited

U.S. PATENT DOCUMENTS

| | | | |
|---|---|---|---|
| 4,027,392 A | 6/1977 | Sawyer et al. | |
| 5,030,236 A | 7/1991 | Dean | |
| 5,292,252 A | 3/1994 | Nickerson et al. | |
| 5,607,426 A | 3/1997 | Ralph et al. | |
| 5,738,521 A | 4/1998 | Dugot | |
| 6,034,295 A * | 3/2000 | Rehberg et al. | 623/23.49 |
| 6,120,502 A * | 9/2000 | Michelson | 606/247 |
| 6,605,089 B1 | 8/2003 | Michelson | |
| 2004/0243207 A1* | 12/2004 | Olson et al. | 607/116 |
| 2006/0276870 A1* | 12/2006 | McGinnis | 607/145 |
| 2008/0125637 A1* | 5/2008 | Geist et al. | 600/372 |

OTHER PUBLICATIONS

I. Yasuda, "Fundamental aspects of fracture treatment", J. Kyoto Med. Assoc. 4: 395-406, 1953, reprinted in Clin Orthop Relat Res., (124):5-8, May 1977.
K. S. McLeod, C. T. Rubin, "The effect of low frequency electrical fields on osteogenesis", J. Bone Joint Surg. 74a:920-929, 1992.
E. Fukada, I. Yasuda, "On the piezoelectric effect of bone", J. Physiol. Soc. Jpn., 12: 1158-62, Oct. 1957.
Fitzsimmons et al., "Frequency dependence of increased cell proliferation" etc., J. Cell Physiol. 139:586-591, 1989.

* cited by examiner

*Primary Examiner* — Christopher D Koharski
*Assistant Examiner* — Natasha Patel
(74) *Attorney, Agent, or Firm* — John S. Hale; Gipple & Hale

(57) ABSTRACT

The present invention relates to the electrical stimulation of bone growth utilizing implantable bone fixation devices and implants to which are attached a screw of nonconductive material powered by a battery for the purpose of creating an electrical-magnetic field to promote bone healing and bone formation. The electric magnetic field is directed to the bone around the device through a battery of a rechargeable type and can include a radio frequency identification device. A constant current is generated in a range of 5-20 micro amperes to stimulate bone healing and bone formation.

11 Claims, 16 Drawing Sheets

20μA CONSTANT CURRENT SOURCE

ELECTRICAL SCREW

RELATED APPLICATIONS

This is an application claiming priority from U.S. Provisional Application No. 60/907,622 filed Apr. 11, 2007.

STATEMENT REGARDING FEDERALLY SPONSORED RESEARCH OR DEVELOPMENT

Not applicable.

REFERENCE TO SEQUENCE LISTING, A TABLE OR A COMPUTER PROGRAM LISTING COMPACT DISC APPENDIX

None.

BACKGROUND OF THE INVENTION

1. Field of Invention

The present invention is generally directed toward a battery powered implantable bone growth stimulator and more specifically to a threaded screw made of nonconductive material upon which a hermetically sealed battery casing is mounted to provide electrical stimulation for bone growth.

2. Background of the Invention

The present invention is directed toward the electronic stimulation of bone (osteogenesis) through or around an orthopedic bone fixation device with an attached implantable bone growth stimulator. It has long been known that the application of electric currents (electric stimulation) can speed bone growth and healing. The electronic stimulation of bone growth has been used in the treatment of fractures, nonunion of bone and to hasten rates of bone fusion as early as the 1800's. Yasuda, in the 1950's in Japan studied the effect of electricity in the treatment of fractures. E. Fukudain "On the piezoelectric effect of bone", J Physiol. Soc. Jpn. 12:1158-62, 1957, and Yasuda, J. Kyoto Med. Assoc. 4: 395-406, 1953 and showed that electric signals could enhance fracture healing. Both direct current capacitively coupled electric fields and alternately pulsed electro magnetic fields affect bone cell activity in living bone tissue.

Bone has bioelectrical properties with naturally occurring generated stress potentials. When the bone is stressed, it will carry an electropositive charge on the convex side and an electronegative charge on the concave side. Wolff's Law demonstrates that bone will form new bone in areas of compression and bone will be resorbed in areas of tension. This biological response to stress in bone creates mechanically generated electrical fields or "strain related potentials. Areas of active growth in bones carry an electronegative charge. When a bone fractures, the bone becomes electronegative at the fracture site. On a cellular basis it has been discovered that osteoblasts are activated by electronegative charges. Research on the effects of electrical forces on bone cells in bone formation and healing has demonstrated that bone healing can be hastened and enhanced by electricity. Studies have shown that by implanting an electrical stimulation device and applying an electrical current around the bone, that bone formation is increased around the cathode (negative electrode) and decreased around the anode (positive electrode). Further research of the use of bone growth stimulators has discovered that the optimal current for bone growth with electrical stimulation is believed to be between 5 and 20 micro amperes.

K. S. McLeod and C. T. Rubin in "The effect of low frequency electrical fields on osteogenesis", J. Bone Joint Surg. 74a:920-929, 1992, used sinusoidal varying fields to stimulate bone remodeling. They found that extremely low frequency sinusoidal electric fields (smaller than 150 Hz) were effective in preventing bone loss and inducing bone formation. They also found strong frequency selectivity in the range of 15-30 Hz. Fitzsimmons et al. in "Frequency dependence of increased cell proliferation", J Cell Physiol. 139(3): 586-91, 1985, also found a frequency specific increase in osteogenic cell proliferation at 14-16 Hz.

U.S. Pat. No. 5,292,252 issued Mar. 8, 1994. discloses a stimulator healing cap powered by an internal small battery. The cap can be reversibly attached to a dental implant, and stimulates bone growth and tissue healing by application of a direct current path or electromagnetic field in the vicinity of bone tissue surrounding the implant, after the implant is surgically inserted.

Another dental device described in U.S. Pat. No. 4,027,392 issued Jun. 7, 1972 discloses an embodiment of a bionic tooth powered by a battery including an AC circuit. The microcircuitry indicated by its FIG. 3 is not shown as being incorporated within the cap.

Another related device is disclosed by in U.S. Pat. No. 5,738,521 issued Apr. 14, 1998 which describes a method for accelerating osteointegration of metal bone implants using AC electrical stimulation, with a preferably symmetrical 20 mu·A rms, 60 KHz alternating current signal powered by a small 1.5 V battery. However, this system is not a compact, self-powered stimulator cap, but is externally wired and powered.

Osteogenetic devices are as described in U.S. Pat. No. 6,605,089 issued Aug. 12, 2003 which discloses a self contained implant having a surgically implantable, renewable power supply and related control circuitry for delivering electrical current directly to an implant which is surgically implanted within the intervertebral space between two adjacent vertebrae. Electrical current is delivered directly to the implant and thus directly to the area in which the promotion of bone growth is desired.

U.S. Pat. No. 6,034,295 issued Mar. 7, 2000 discloses an implantable device with a biocompatible body having at least one interior cavity that communicates through at least one opening with the surrounding body so that tissue surrounding the implantable device can grow through the opening. Two or more electrodes are contained within the device having terminals for supplying a low-frequency electrical alternating voltage and at least one of which is located inside the cavity. U.S. Pat. No. 5,030,236 issued Jul. 9, 1991 also discloses the use of electrical energy that relies upon radio frequency energy coupled inductively into an implanted coil to provide therapeutic energy. However, none of these devices perform satisfactory osteogenesis promotion, while leaving the implant member or stem essentially unchanged in appearance and mechanical properties.

The art that relates specifically to bone growth stimulation by small, self powered electrical means is very limited and most of the bone graft stimulation has been undertaken using power sources located outside the patient's body. Another problem that occurs when the implant is self powered is that the power short circuits against the metal screw or device.

There is thus a widely recognized need for a practical, self-powered osteogenesis implant that can generate electrical stimulation signals. It would also be extremely advantageous that such implants, when used for example in hip or knee implants, should require minimal changes to both appearance and mechanical integrity and function of the implants. The primary goal of such devices would be to increase bone density and implant bone contact ratio around any new implant as a routine common clinical practice.

SUMMARY OF THE INVENTION

According to the present invention there is provided an osteogenesis device including an implant member in the nature of a nonconductive screw having a battery cap mounted thereto to provide electrical signals from the cap to the tip of the screw to function as an electrical bone growth stimulation device. In another embodiment, a universal cap mount with an internal electrical source is mounted on a standard pedicle screw to provide electrical bone growth.

It is still another object of the invention to provide a self container power source and generating circuit in the implant.

It is yet another object of the invention to provide a powered electrical screw implant which does not short out when used for electrical stimulation.

It is another object of the present invention to provide an electrical bone growth promotion implant in which an active cathode is fully contained within the bone fusion mass.

It is a further object of the invention to provide a method of fixation of fractures that not only stabilizes the bone but also enhances bone healing with the use of electricity that can be applied through or around the implant.

It is yet another object of the invention to provide an implant to which a bone growth stimulator can be attached to enhance bone formation at spinal fusion sites.

It is still another object of the invention to provide a self powered implant with a tissue-contacting body having an external surface in contact with biological tissue and having a hollow enclosure, a conductive element in electrical communication with the hollow enclosure and electrically isolated from the external surface, and an electrical stimulation mechanism located within the hollow enclosure for providing electrical stimulation to the biological tissue through the conductive element.

It is yet another object of the present invention to provide an electrical bone growth promotion implant in which the power source can be wholly or partially supplied or recharged by externally applied sources;

It is another object of the invention to provide an implantable bone growth stimulator implant that can be attached to an intramedullary nail or rod to enhance bone formation and healing at fracture or fusion sites.

It is still another object of the invention to provide an implantable bone growth stimulator that can provide a D. C., constant current source.

It is yet a further object of the present invention to provide an implantable bone growth stimulator that can be attached to an orthopedic implant in combination with an internal or external implantable cathode and anode that are sized to enhance bone growth stimulation.

It is another object of the present invention to provide an implantable fixation implant for cooperation with an internal power supply where the fixation implant serves to treat avascular necrosis;

It is still another object of the invention to provide an implantable bone growth stimulator and orthopedic implant to which a radio frequency identification device can be embedded or attached.

These and other objects, advantages, and novel features of the present invention will become apparent when considered with the teachings contained in the detailed disclosure along with the accompanying drawings.

DETAILED DESCRIPTION OF THE INVENTION

The best mode and preferred embodiment of the present invention is shown in FIGS. 1-8. The cannulated threaded screw 20 is preferably manufactured out of a non-electrically conductive material such as the non-bioabsorbable polymer PEEK (Polyther-ether-ketone) or other type of hardened material such as ceramic, PSU (polysulphone) or PEKK (Polyether-ketone-ketone) or compositions of the same or any of a wide variety of suitable poly (ether-co-ketone) materials which are commercially available. Because the screw is insulated (nonconductive material or conductive material with nonconductive material to the tip, the current flows around the screw from the insert to the tip of the insert and does not actually flow through the screw which prevents shortage of current which is different from other electrical stimulation devices.

Alternatively, the cannulated threaded screw 20 can be manufactured out of conductive material such as stainless steel, titanium, titanium alloys or other conductive metal or allograft cortical bone with an inner insulated sleeve which is inserted through the screw lumen.

Figure 4:
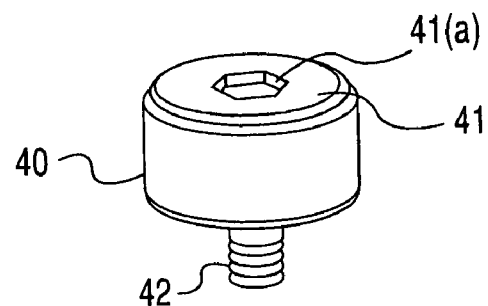
FIG. 4 is perspective view of the battery cap housing.
Figure 5:
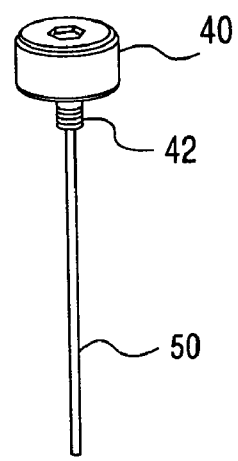
FIG. 5 is a perspective view of the cathode mounted in the cap housing stem.
Figure 6:
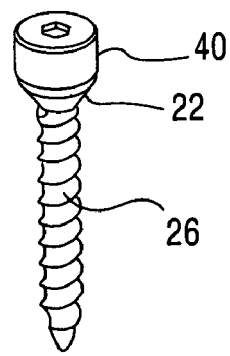
FIG. 6 is the assembled electrical screw assembly.
Figure 7:
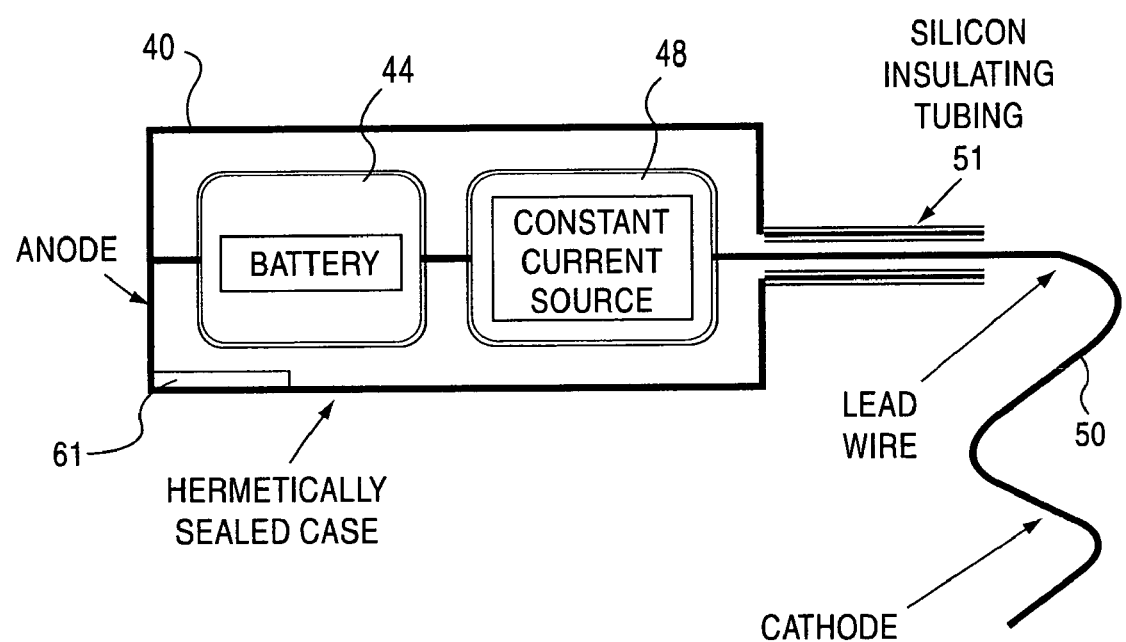
FIG. 7 is a schematic of the battery casing, current circuit and lead wire.

The electrical threaded screw 20 is preferably constructed of non conductive material as previously described with a head 22 defining torque receiving means in the nature of a cutouts 25 which may be four or more in number with a threaded shank 26 extending therefrom. The shank defines a through going lumen 28 which is centrally axially located within the shank and has external threads 30 formed along at least a portion of the shank. The head 22 also defines a chamber 32 at the proximal end of the lumen 28 which is threaded to receive a threaded stem 42 of battery casing 40 as is shown in FIG. 4. If desired the chamber 32 can be formed to fit a snap casing stem 43 such as that shown in FIG. 2.

Figure 8:
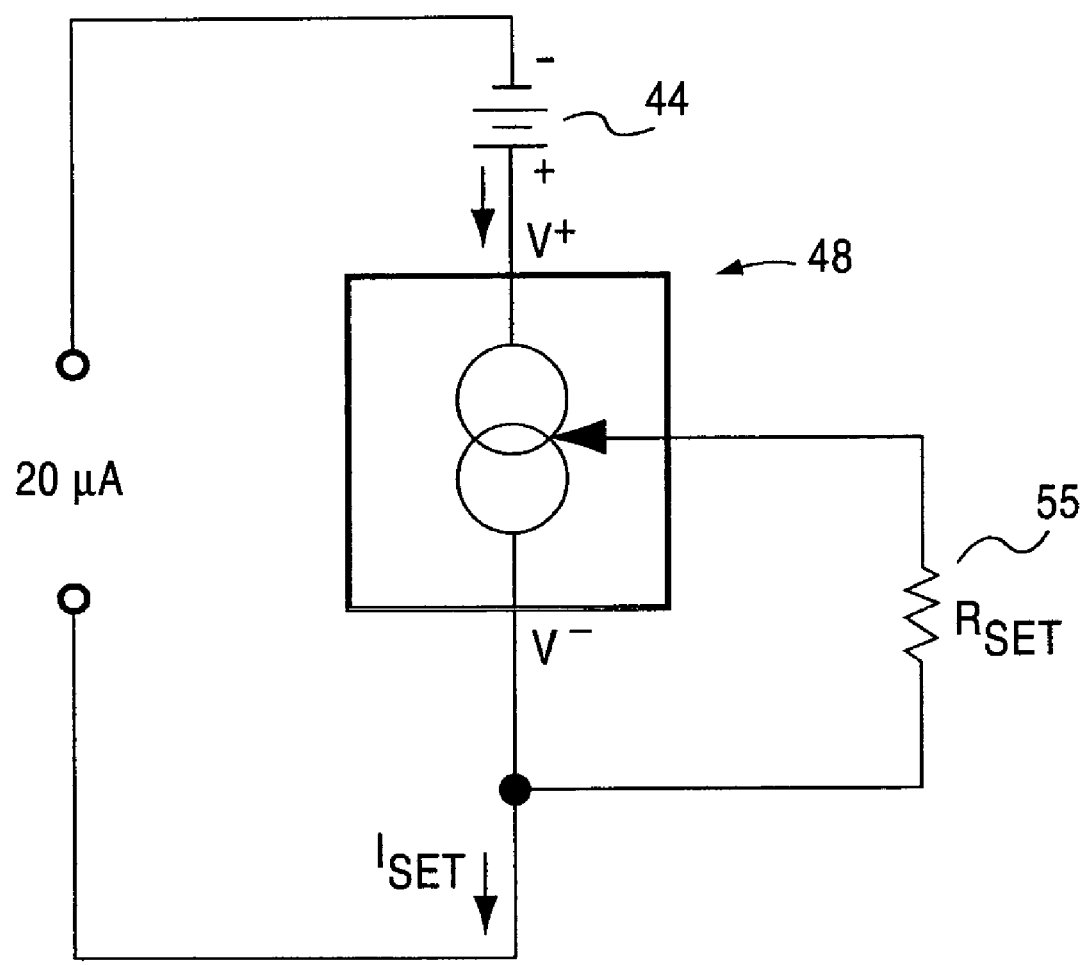
FIG. 8 is an electrical diagram of the circuit constant current source.

The casing 40 is preferably disc shaped and hermetically sealed. The casing 40 is formed with a housing 41 and a cap 49 which is press mounted over the housing 41. Mounted in the housing 41 is an integrated circuit board 45 and a battery 44 which is electrically connected to a chip 46 which has a circuit 48 as shown in FIG. 8. The battery 44 is held in place by battery clip 54 and a sealing ring 56 and sealing top member 58 are held in place by leaf spring 59 when the cap 49 is mounted over housing 41. The circuit board 45 provides a constant current source via connector member 57 to a cathode lead wire 50 which is encased in a silicon insulating tube 51. The lead wire and insulating tube 51 are positioned through the lumen 28 of screw shank 26 so that the tip 52 of the cathode extends outside of the shank body. The current which is produced ranges between 5 and 50 micro amperes with the preferred range being between 5 and 20 micro amperes and the most preferred range is 20 micro amperes. Rechargeable lithium batteries are an alternative way to power the bio-implantable microsystem. Power is delivered remotely to charge the implanted battery which eliminates the necessity for battery replacement. Thus the tip 52 acts as a cathode and the casing 40 acts as an anode.

The circuit diagram shown in FIG. 8 shows a representative current of 20 micro amperes which can be modified as desired by changing the resistor 55 in the circuit and the case housing forms the anode for the circuit. An RFID chip can be mounted in the casing 40 allowing easy identification of the implant outside of the patient's body with the additional benefit that it can be used to power the implant. The electrical screw assembly when implanted in the bone and set to generate a current of 20 micro amperes is particularly effective in the treatment of avascular necrosis.

Alternatively the present invention can use a signal conditioning circuit for a remotely rechargeable system. A rechargeable lithium ion battery powers this circuit. The desired output, then goes directly to the electrodes. A second rechargeable lithium ion battery may be included to serve as a back up and in this embodiment a lithium ion charging chip is included which is connected to the designed integrated circuit through a logic interface. The two batteries would work in tandem thus when one battery powers the integrated circuit, the other battery gets recharged and vice versa providing an uninterruptible output. The integrated circuit optionally can use a series of charge pumps or transistors to get the required boost in voltage. This alternate integrated circuit uses voltage detector circuits to detect battery voltages, has a voltage regulator, pulse generator circuits, logic circuits and requisite switches.

The top surface 41 of cap 49 is flat and is provided with an angular cutout 41(a) which allows torque to be generated by an outside tool driving the threaded stem 42 into the screw head chamber 32 so that it is securely mounted to the head of the screw.

Figure 1:
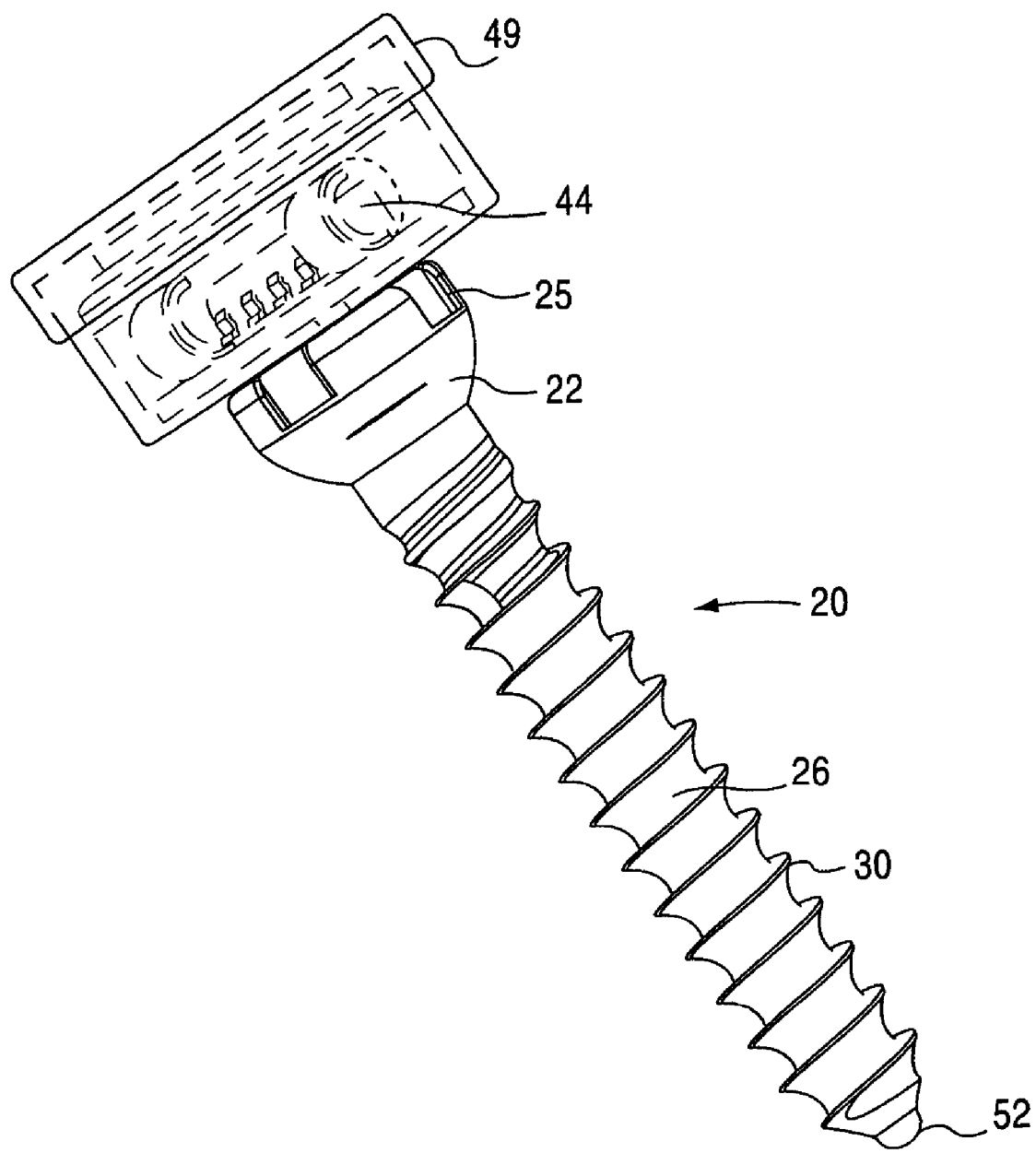
FIG. 1 is a perspective view of the inventive electrical bone screw assembly with component cap parts shown in phantom.
Figure 2:
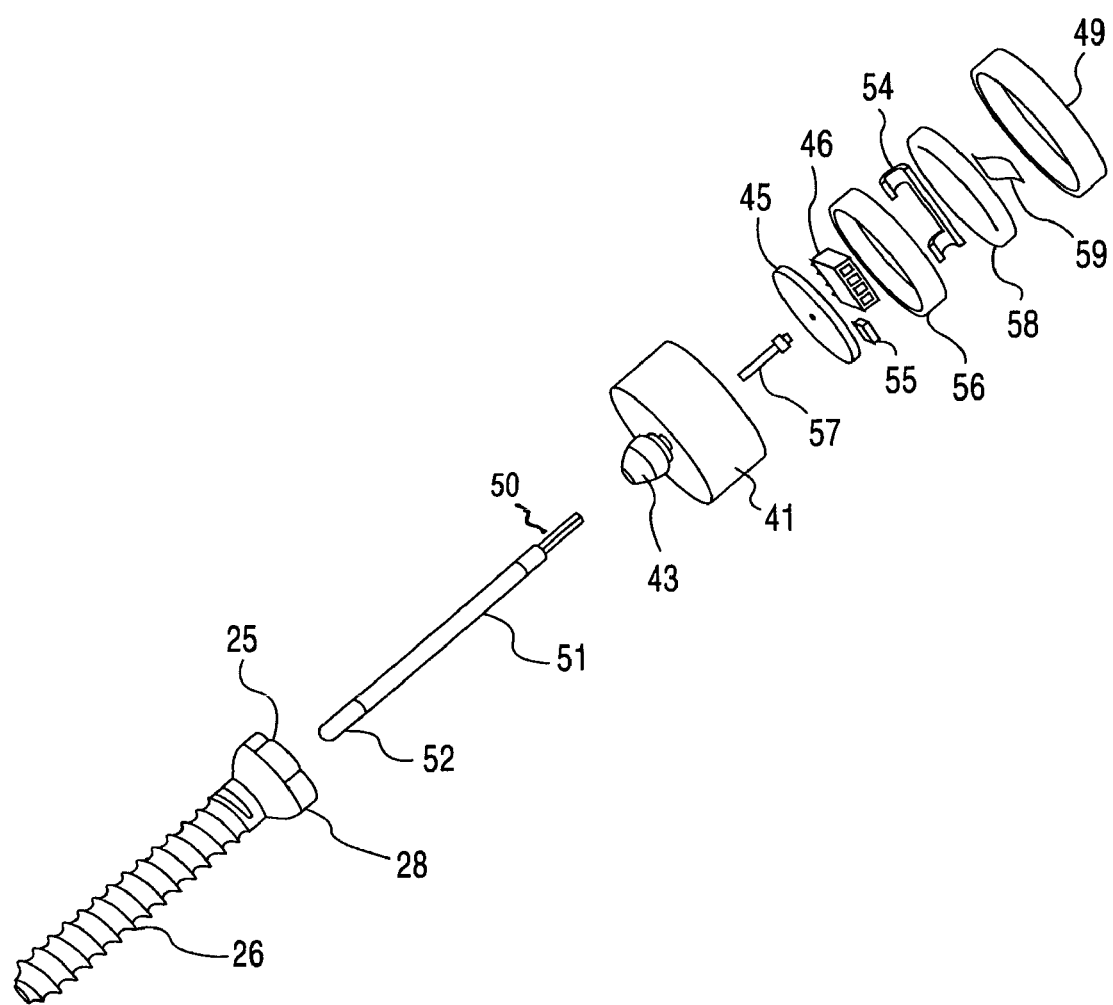
FIG. 2 is an exploded view of the bone screw assembly of FIG. 1.
Figure 3:
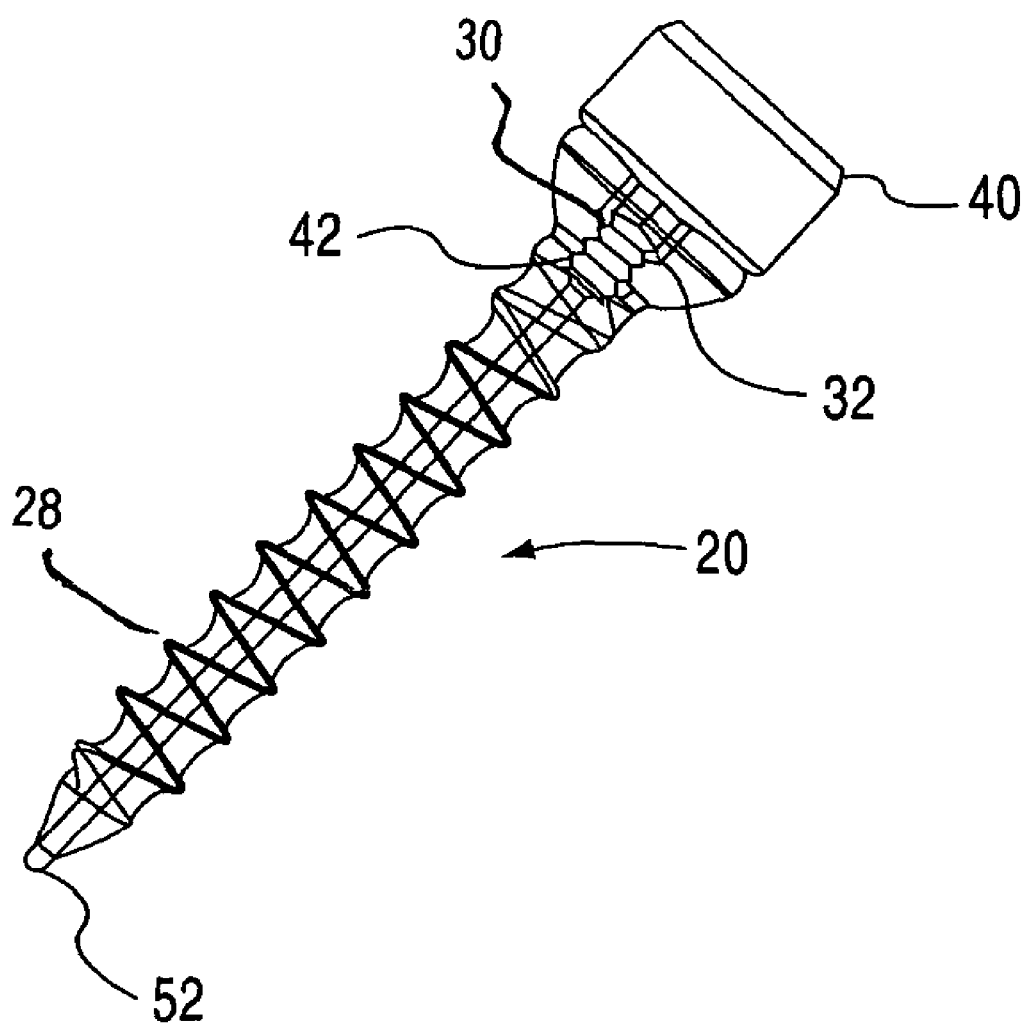
FIG. 3 is a perspective view of the electrical bone screw assembly shown in FIG. 1 showing the cap casing stem threadably mounted in the screw head and the cathode mounted in the lumen of the screw shaft.
Figure 9:
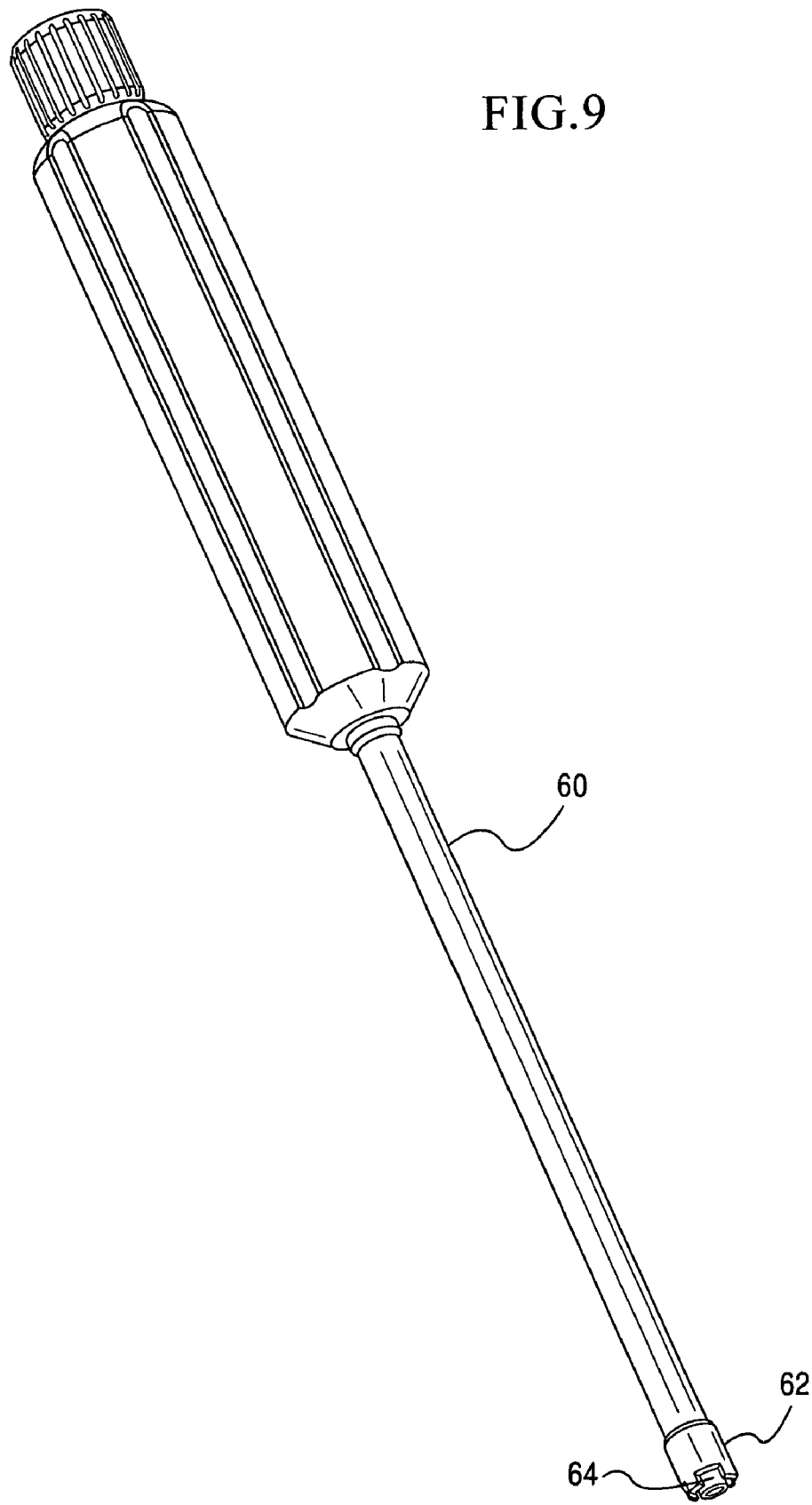
FIG. 9 is a perspective view the driver used to insert the electrical bone screw.
Figure 10:
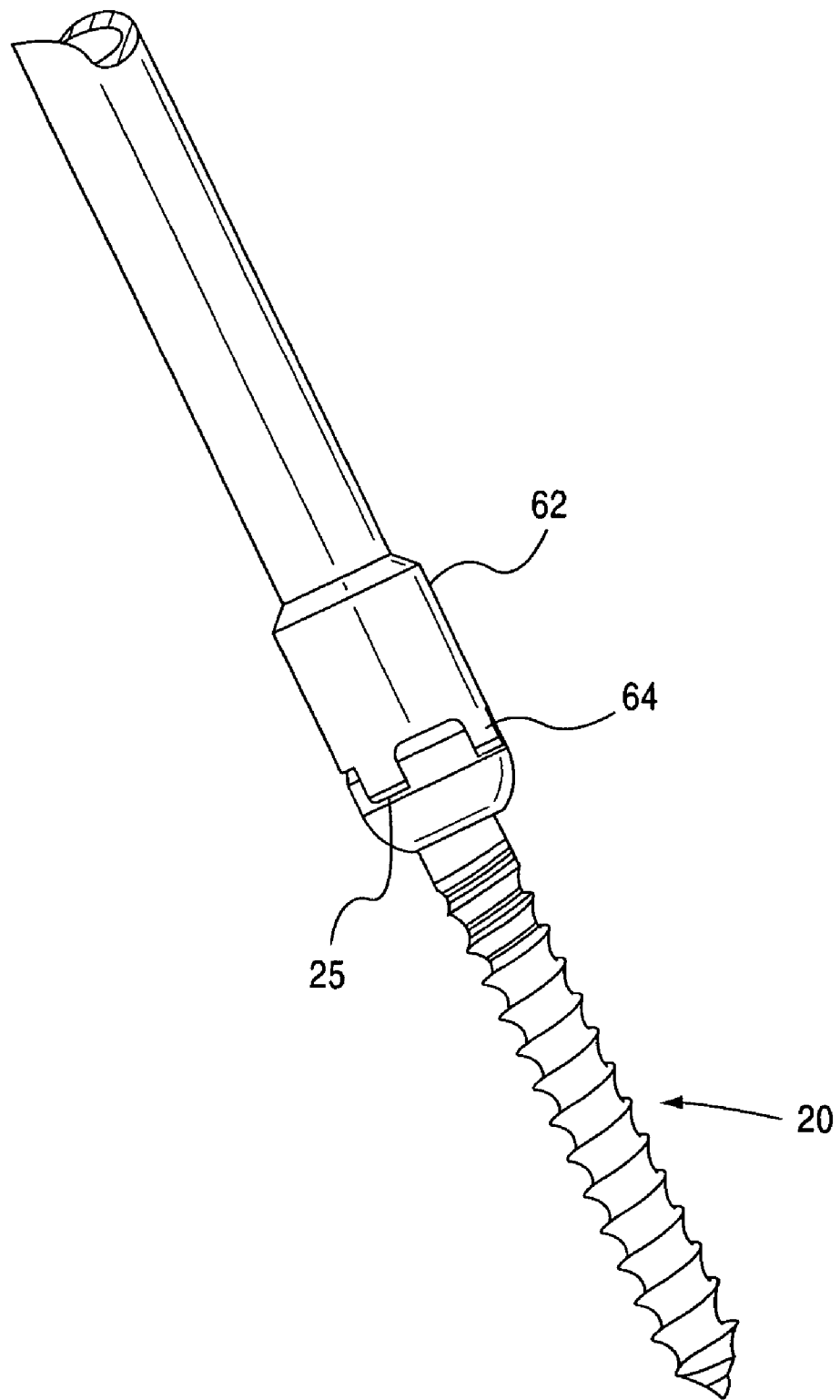
FIG. 10 is an enlarged view of the driver tip of the driver shown in FIG. 9 inserted into the screw head to apply torque to the screw.

As can be seen in FIGS. 9 and 10 a driver 60 is formed with an end 62 having projections 64 which fit in the cutouts 25 of the screw head so that torque can be applied to the screw head driving the screw into the bone of the patient. Once the screw has been implanted into the patient, the battery casing 40 and associated cathode 50 are mounted to the screw 20 by applying torque with a tool mounted in cutout 41(a) and screwing the stem 42 into threaded chamber 32 or pushing the stem 43 as shown in FIG. 2 into a snap on chamber formed in screw head 22. The device then provides an electrical current through the portion of the patients bone which is fractured or has a defect to promote bone growth.

Figure 11:
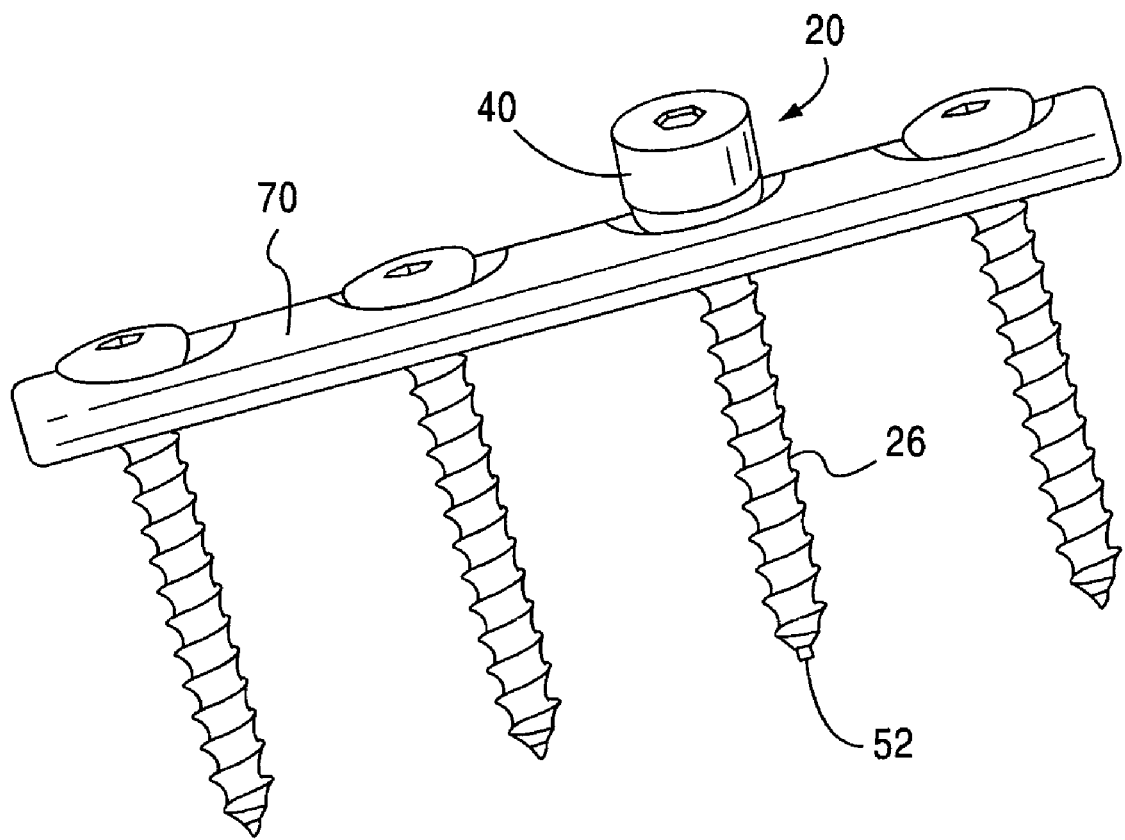
FIG. 11 is a perspective view of the bone growth stimulator assembly attached to an internally threaded screw mounted in a bone plate.
Figure 12:
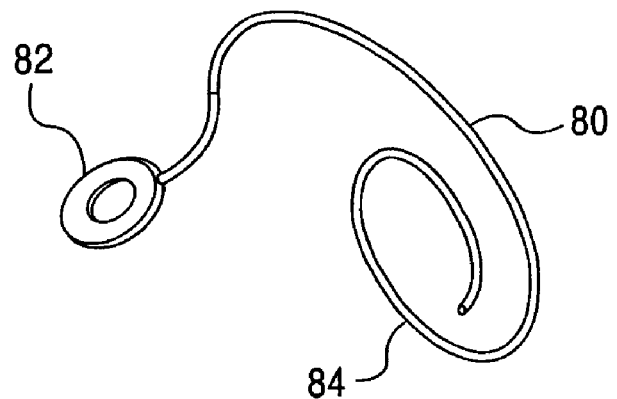
FIG. 12 is a perspective view of an external lead which can be mounted on the electrical screw assembly forming a cathode.
Figure 13:
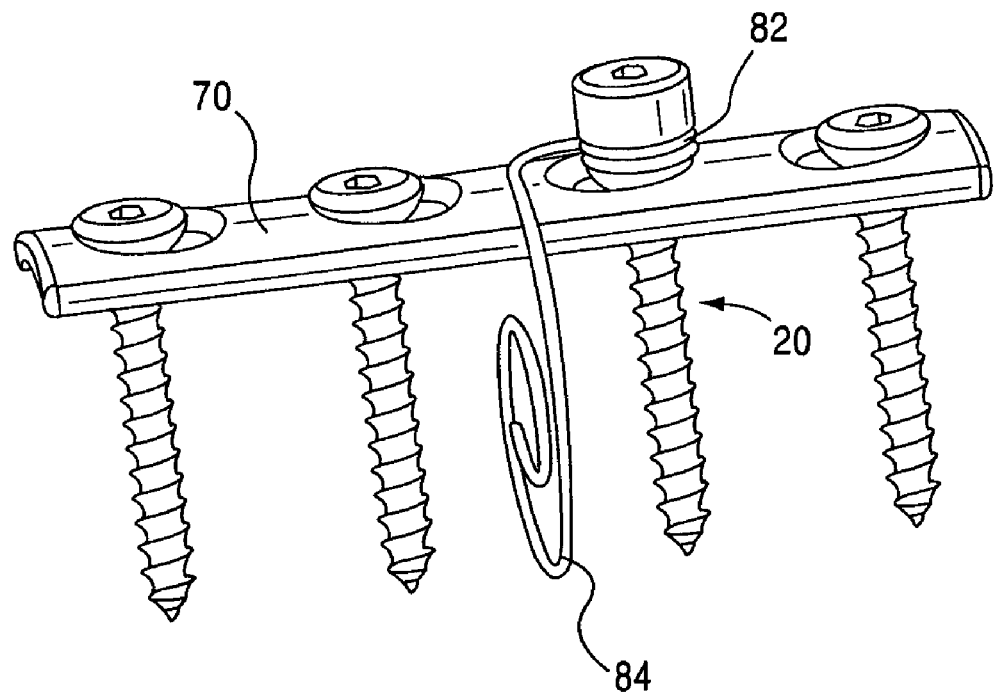
FIG. 13 is a perspective view of the external cathode lead shown in FIG. 12 attached to the electrical screw assembly shown in FIG. 11.

The electrical screw assembly 20 can be used in connection with a bone plate 70 as shown in FIGS. 11 and 13. In the usage shown in FIG. 13 an external lead 80 is formed with an electrically conductive washer 82 secured to one and having a spiral section 84 at the distal end. The washer 82 is mounted between the screw 20 and casing 40 as shown in FIG. 13. The lead wire 84 can have one or more sections insulated to provide variances in the electrical field. The washer 82 is mounted around stem 42 and is positioned between the casing 40 and the top surface of the screw head 22 so that the external spiral lead wire 84 extends past the bone plate 70 allowing a primary electrical field to be formed between the cathode spiral lead wire and the anode of the casing.

The electrical screw assembly 20 can also be used in connection with a pedicle screw electrical stimulation device 90 as seen in FIGS. 14-18. As seen in FIGS. 14-18, the device 90 has a flexible support mount 92 which fits over and can be universally attached to any make of pedicle screw 200 seen in FIG. 14 as being screwed into adjacent vertebrae 300.

Figure 14:
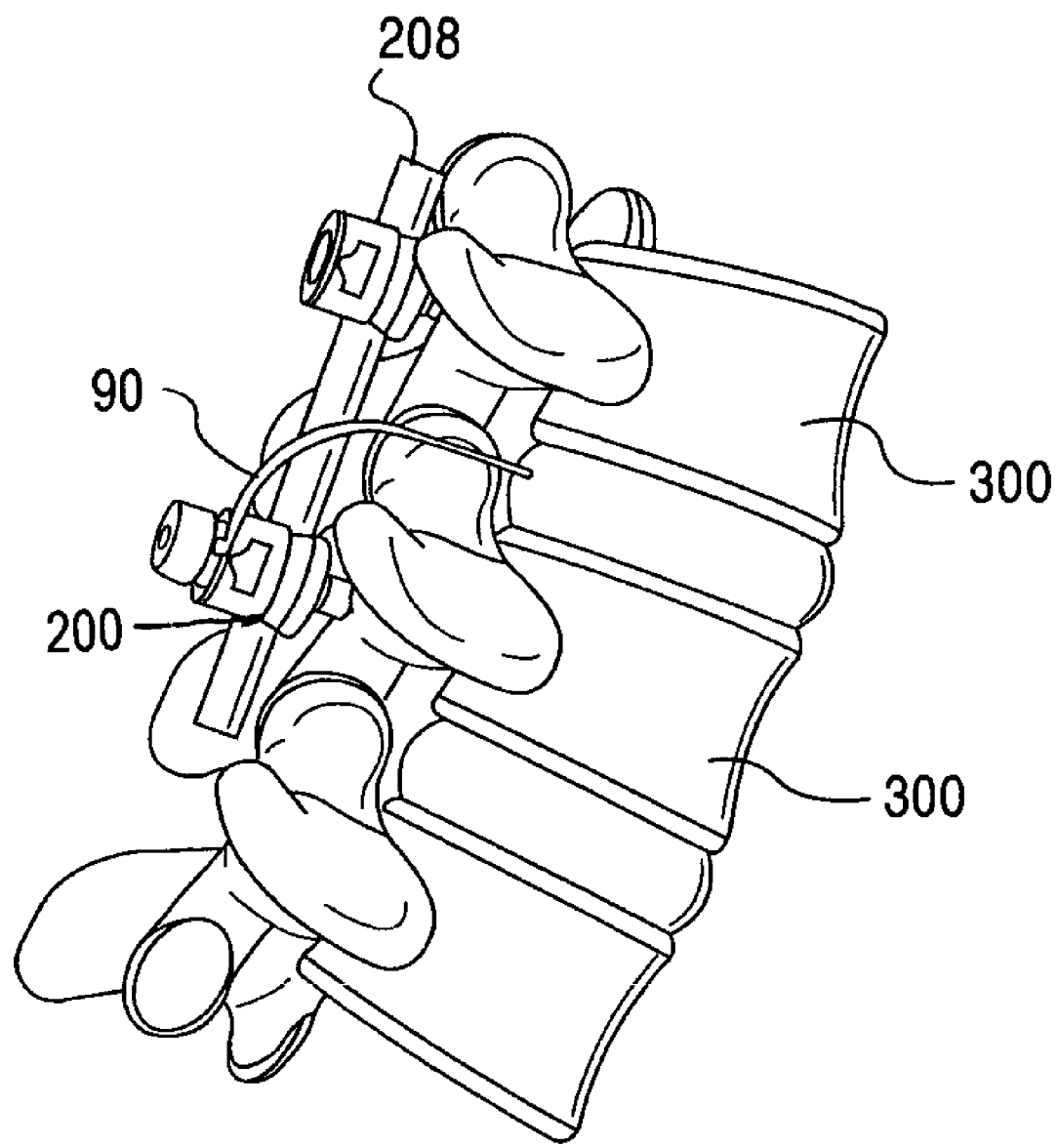
FIG. 14 is a perspective view of an inventive pedicle screw electrical stimulation device using the cathode lead shown in FIG. 12 mounted to spinal vertebrae.
Figure 15:
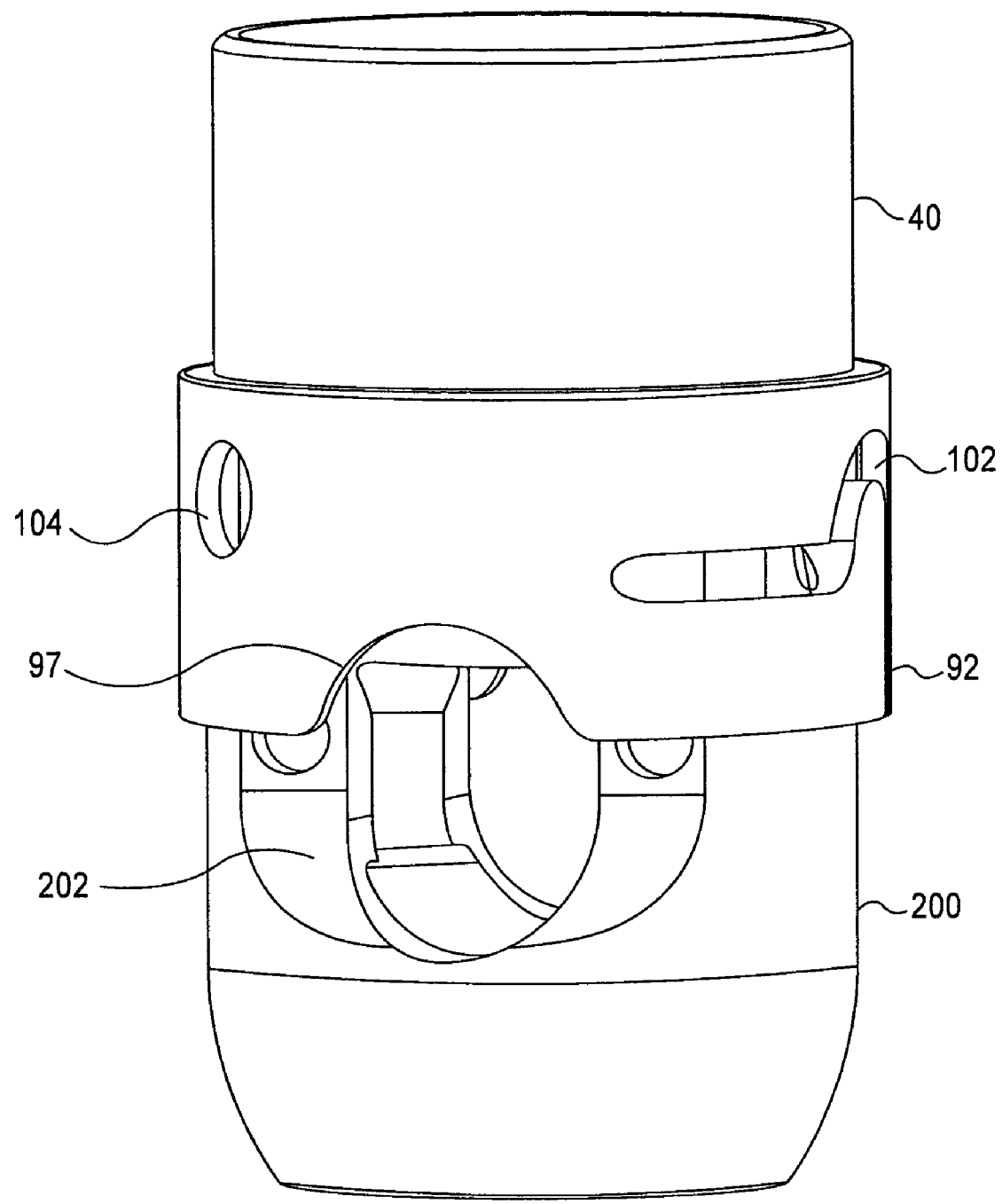
FIG. 15 is an enlarged view of the pedicle screw electrical stimulation device of FIG. 14.
Figure 16:
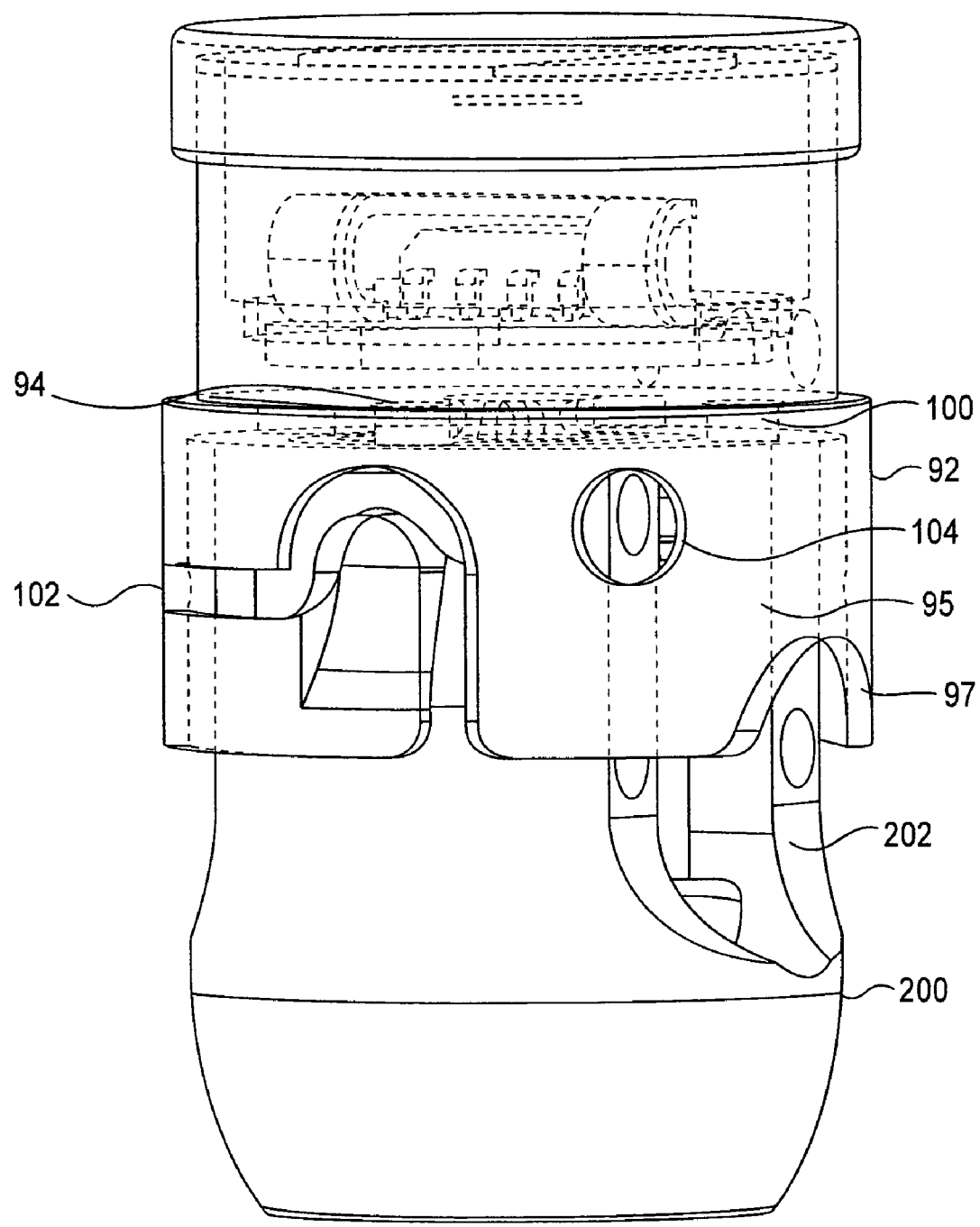
FIG. 16 is a perspective view of the pedicle screw electrical stimulator device of FIG. 15 showing the universal mount and battery casing in phantom.
Figure 17:
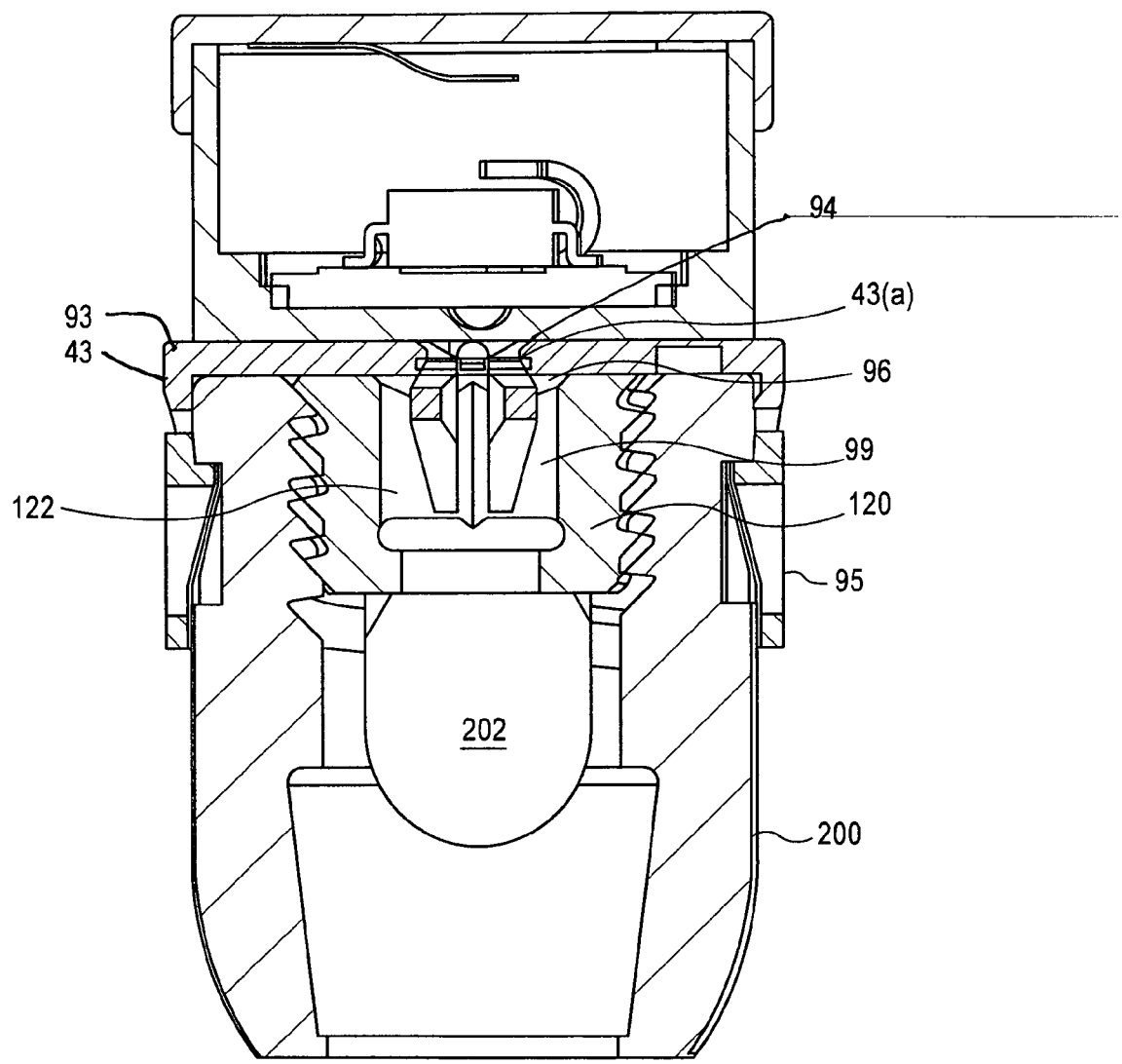
FIG. 17 is a cross sectional view of the pedicle screw electrical stimulation device of FIG. 15.
Figure 18:
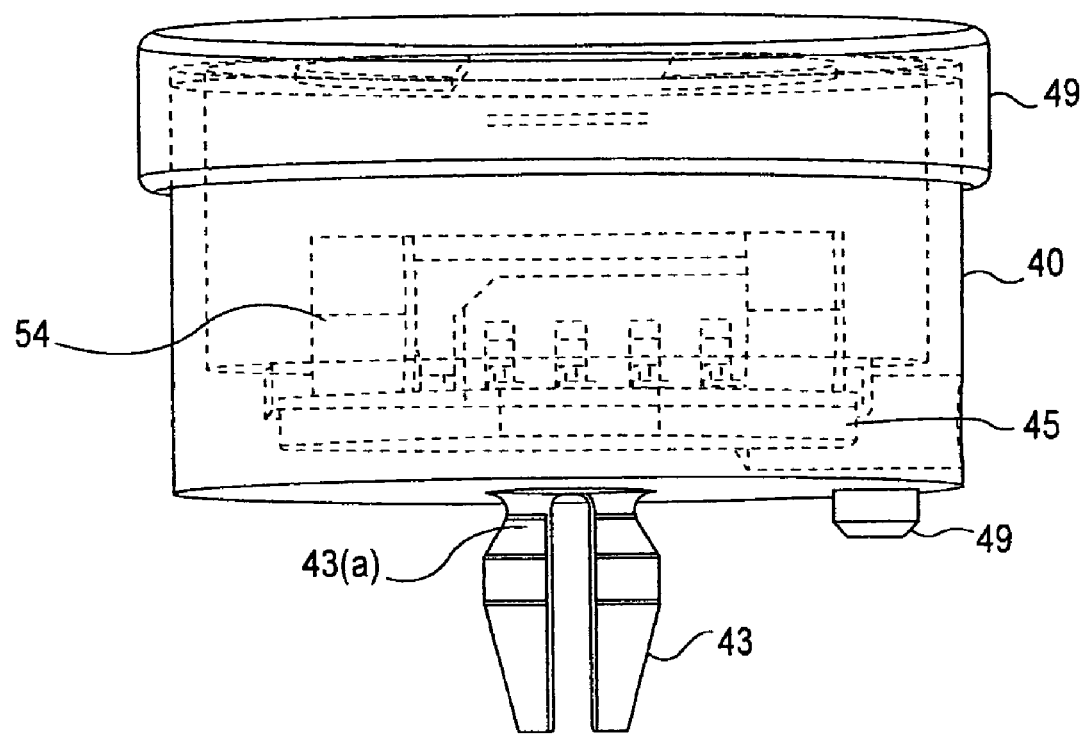
FIG. 18 is a view of the battery cap of FIG. 15 with elements shown partially in phantom.
Figure 19:
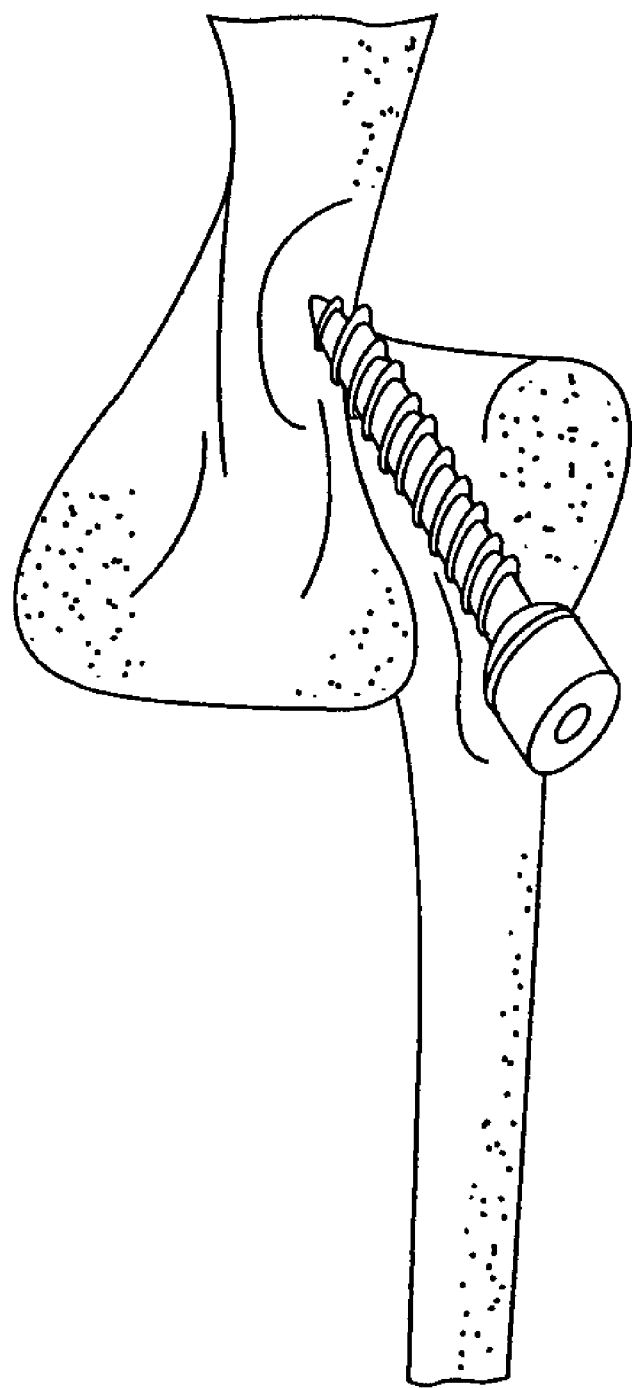
FIG. 19 is a schematic showing the inventive surgical screw used in the hip to treat vascular necrosis.

The support mount 92 is in the form of a base mount member 93 with a central aperture 94 defined in the top surface which receives the snap lock stem 43 of cap member 40. The base mount member 93 has an inwardly projecting flexible rim assembly 96 which is cammed outward by the action of the stem 43 which is forced into it and snaps back against the lesser diameter of the stem 43(a) to hold the stem 43 in fixed position within the chamber 99 formed by an insert member 120. Surrounding the central aperture 94 are a plurality of locking recesses 100 as shown in FIG. 16, which additionally act as spacers and can selectively receive and hold the lock button 49 of the battery casing 40 as best shown in FIG. 18 so that the battery casing 40 cannot be rotated on the top of the pedicle screw 200. The side wall 95 of the base mount member 93 extends down over the head of the pedicle screw 200 and is formed with a curved cut away channel 102 and a viewing aperture 104 which allows the support mount to be flexibly mounted over the top of the pedicle screw. The cut away channel 102 is best seen in FIGS. 15 and 16. The base mount member 93 additionally defines curved cutouts 97 which fit over a support rod 208 as shown in FIG. 14 holding the support rod 208 in place in the pedicle screw transverse bore 202. A threaded interior insert 120 as seen in FIG. 17 is threaded in the pedestal screw 200 and is used to lock the stem 42/43 of battery casing 40 to the pedicle screw 200. As shown in FIG. 17, the threaded insert 120 defines a chamber 122 which receives a snap on stem 43 to hold the battery casing 40 in a fixed mounted position. An electrical field is generated between the anode and cathode to accelerate bone growth of the fractured vertebrae. The support mount 92 can also be mounted onto an intramedullary nail, pedicle screw rod, surgical plate, surgical washer or plate rod.

The principles, preferred embodiments and modes of operation of the present invention have been described in the foregoing specification. However, the invention should not be construed as limited to the particular embodiments which have been described above. Instead, the embodiments described here should be regarded as illustrative rather than restrictive. Variations and changes may be made by others without departing from the scope of the present invention as defined by the following claims:

What I claim is:

1. An osteogenesis device for providing electrical stimulation in bone comprising: a screw member having proximal and distal ends, said screw member being constructed of an electrically non-conductive material with an external threaded portion, said screw threaded portion being constructed essentially entirely from a group of materials consisting of ceramic, non-conductive plastic consisting of PEEK (Poly-ether-ketone), PSU (polysulphone), PEKK (Polyether-ketone-ketone) or polyether-co-ketone, said screw member defining an axial through going lumen, a hermetically sealed battery casing removably mounted on a proximal end of said screw member, a battery mounted in said battery casing and circuit means connecting said battery to a lead wire, said lead wire being mounted in said lumen and extending through said lumen beyond a distal tip of said screw member acting as a cathode.

2. The device of claim 1 wherein said battery casing is formed with torque receiving means.

3. The device of claim 1 wherein said battery casing has a stem extending therefrom and is removably mounted on said implant member.

4. The device of claim 1 wherein said battery generates a constant current source in the range of about 1 to about 50 micro amperes.

5. The device of claim 1 wherein said battery generates a constant current source in the range of 5-20 micro amperes.

6. The device of claim 1 including a radio frequency identification chip including unique identifying information embedded into said surgical implant member that can relay information to an external receiver and/or be used to power the circuit of the implant.

7. An osteogenesis device for providing electrical stimulation in bone comprising: a screw constructed of an electrically non-conductive material with a body defining a lumen and provided with an external threaded portion and a hermetically sealed battery casing removably mounted to said screw, a battery mounted in said battery casing and circuit means connecting said battery to a lead wire, said lead wire being fixed within said lumen formed in said screw and projecting beyond a distal tip of said screw serving as a cathode, said screw threaded portion being constructed from a group of non-conductive ceramic plastic materials consisting essentially entirely of PEEK (Poly-ether-ketone), PSU (polysulphone), PEKK (Polyether-ketone-ketone) or polyether-co-ketone.

8. The osteogenesis device of claim 1 wherein said implant member defines a lumen and said lead wire is fixedly mounted to said lumen and extends past said distal end.

9. The osteogenesis device of claim 1 wherein said battery is provided with means allowing it to be recharged by induced current.

10. The osteogenesis device of claim 7 wherein an RFID chip is mounted to said implant member, said RFID chip containing data about the implant member.

11. A osteogenesis device of claim 7 wherein said battery is provided with means allowing it to be recharged by induced current.

* * * * *